United States Patent [19]

Ueno et al.

[11] Patent Number: 5,256,696
[45] Date of Patent: Oct. 26, 1993

[54] TREATMENT OF CARDIAC DYSFUNCTION WITH 15-KETOPROSTAGLANDIN COMPOUNDS

[75] Inventors: Ryuji Ueno; Hiroyoshi Osama, both of Hyogo, Japan

[73] Assignee: Kabushikikaisha Ueno Seiyaku Oyo Kenkyujo, Osaka, Japan

[21] Appl. No.: 892,640

[22] Filed: Jun. 2, 1992

Related U.S. Application Data

[63] Continuation of Ser. No. 616,952, Nov. 21, 1990, abandoned.

[30] Foreign Application Priority Data

Nov. 22, 1989 [JP] Japan .................. 1-303840

[51] Int. Cl.$^5$ .................. A61K 31/19; A61K 31/557
[52] U.S. Cl. .................. 514/573
[58] Field of Search .................. 514/573

[56] References Cited

U.S. PATENT DOCUMENTS

| | | | |
|---|---|---|---|
| 4,639,461 | 1/1987 | Nakane | 514/469 |
| 4,680,288 | 7/1987 | Irmscher et al. | 514/63 |

FOREIGN PATENT DOCUMENTS

| | | |
|---|---|---|
| 0153858 | 9/1985 | European Pat. Off. |
| 281239 | 9/1988 | European Pat. Off. |
| 284180 | 9/1988 | European Pat. Off. |
| 289349 | 11/1988 | European Pat. Off. |
| 292177 | 11/1988 | European Pat. Off. |
| 308135 | 3/1989 | European Pat. Off. |
| 310305 | 4/1989 | European Pat. Off. |
| 330511 | 8/1989 | European Pat. Off. |
| 342003 | 11/1989 | European Pat. Off. |
| 343904 | 11/1989 | European Pat. Off. |
| 345951 | 12/1989 | European Pat. Off. |
| 2328132 | 1/1975 | Fed. Rep. of Germany . |
| 164512 | 4/1983 | Japan . |
| 163365 | 4/1984 | Japan . |

OTHER PUBLICATIONS

Medicinal Chemistry, 3rd ed. Alfred Burger, ed. Wiley-Interscience, N.Y. (1970) pp. 71-72, 74-75.
STN File Server & File CA & Chemical Abstracts, vol. 98, No. 11, abstract No. 84144J, Columbus, Ohio, US; US; H. J. Mest et al.: "Influence of 15-keto-metabolites and 13,14-dihydro-15-keto-metabolites of PGE2 and PGF2. alpha. as well as of 6-keto-PGF1.alpha. as a metabolite of PGI2 on aconitine induced cardiac arrhythmia in rats", & ACTA Biol. Med. Ger., 41(9), 819-22, 1982.
Patent Abstracts of Japan, vol. 7, No. 171 (C-178)[1316], Jul. 28th, 1983; & JP-A-59 79 973 (Ono Yakuhin Kogyo K.K.) May 13, 1983.
STN File Server & File CA & Chemical Abstracts, vol. 102, No. 1, abstract No. 1100u, Columbus, Ohio, US; P. Conzen et al.: "Hypoxic pulmonary vasoconstriction and endogenous prostaglandin (PG) and thromboxane (TX) release in anesthetized pigs", & Biomed. Biochim. Acta, 43 (8-9), 265-8, 1984.
Actor Phys. Scand., vol. 66, Oct. 3rd, 1966, pp. 509-510; E. Anggard: "The biological activities of three metabolites of prostaglandin E".

*Primary Examiner*—Frederick E. Waddell
*Assistant Examiner*—William Jarvis
*Attorney, Agent, or Firm*—Sughrue, Mion, Zinn, Macpeak & Seas

[57] ABSTRACT

A method for treatment of a cardiac dysfunction which comprises administering, to a subject in need of such treatment, a 15-ketoprostaglandin compound in an amount effective in treatment of the cardiac dysfunction.

14 Claims, No Drawings

TREATMENT OF CARDIAC DYSFUNCTION WITH 15-KETOPROSTAGLANDIN COMPOUNDS

This is a continuation of application Ser. No. 07/616,952, filed Nov. 21, 1990, now abandoned.

BACKGROUND OF THE INVENTION

1. Field of the Invention

The present invention relates to a method for treatment of a cardiac dysfunction which comprises administering a 15-ketoprostaglandin compound to a subject.

Prostaglandins (hereinafter, prostaglandins are referred to as PGs) are members of a class of organic carboxylic acid that are contained in human and most other mammalian tissues or organs and that exhibit a wide range of physiological activities. Naturally occurring PGs possess as a common structural feature the prostanoic acid skeleton:

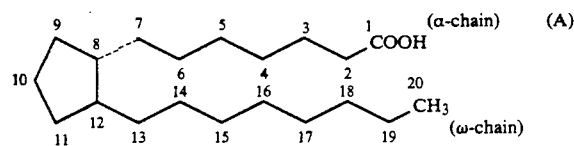

Some synthetic analogues have somewhat modified skeletons. The primary PGs are classified based on the structural feature of the five-membered cycle moiety into PGAs, PGBs, PGCs, PGDs, PGEs, PGFs, PGGs, PGHs, PGIs and PGJs, and also on the presence or absence of unsaturation and oxidation in the chain moiety as:

Subscript 1—13, 14-unsaturated-15-OH
Subscript 2—5,6—and 13,14-diunsaturated-15-OH
Subscript 3—5,6—13,14—and 17,18-triunsaturated-15-OH Further, PGFs are sub-classified according to the configuration of hydroxy group at position 9 into α(hydroxy group being in the alpha configuration) and β(hydroxy group being in the beta configuration).

BACKGROUND INFORMATION

JP-A-164512/1983 discloses the protecting action of 15-cycloalkyl-6-oxo-PGE$_1$, 15-cycloalkyl-PGI$_1$ and I$_2$, 5-cycloalkyl-6,9α-nitrilo-PGI$_1$ and 15-cycloalkyl-6,9α-thio-PGI$_1$ and I$_2$ from disorder of cells (including heart disease). JP-A-203911/1983 discloses the cell-protecting action of certain 6-oxo-PGE$_1$ and PGI$_1$ having methyl group(s) at one or two of positions 15, 16, 17 and 20 and specific 15-cyclopentyl-PGI$_1$. All these compounds, however, do not belong to 15-keto-PGs or their derivatives.

European Patent Application No. 0,310,305 describes that 15-keto-PGs can be used as catharitics.

As a result of extensive studies about the biological properties of 15-ketoprostaglandin compounds, the present inventors have discovered that these compounds are useful as an agent for treating damaged cardiac function.

SUMMARY OF THE INVENTION

In a first aspect, the present invention provides a method for treatment of a cardiac dysfunction which comprises administering, to a subject in need of such treatment, a 15-ketoprostaglandin compound in an amount effective in treatment of the cardiac dysfunction.

In a second aspect, the present invention provides a use of a 15-ketoprostaglandin compound for the manufacture of a medicament for treatment of a cardiac dysfunction.

In a third aspect, the present invention provides a pharmaceutical composition for treatment of a cardiac dysfunction comprising a 15-ketoprostaglandin compound in association with a pharmaceutically acceptable carrier, diluent or excipient.

DETAILED DESCRIPTION OF THE INVENTION

As used herein, the term "cardiac dysfunction" means all conditions having etiology based on or accompanied by insufficiency of cardiac function, which is a symptom or disease based on unbalance between the cardiac output and the periferal demand and most part of which is resulted from disorder of myocardial contractive and dilative functions. Examples of these symptoms or diseases include orthopnea, dyspnea, pulmonary congestion, hepatic congestion, cardipalmus, sensation of precordial compression, heart contusion, arrhythmia, angina pectoris, myocardial infraction, atrial fibrillation, atrial flutter, paroxysmal tachycardia etc.

As used herein, the term "treatment" or "treating" refers to any means of control of a disease in a mammal, including preventing the disease, curing the disease, relieving the disease and arresting or relieving the development of the disease.

The term "15-ketoprostaglandin compounds", referred to as 15-keto-PG compounds, include any prostaglandin derivatives which have an oxo group in place of the hydroxy group at position 15 of the prostanoic acid nucleus irrespective of the presence or absence of the double bond between positions 13 and 14.

Nomenclature

Nomenclature of 15-keto-PG compounds herein uses the numbering system of prostanoic acid represented in formula (A) shown above.

While formula (A) shows a basic skeleton having twenty carbon atoms, the 15-keto-PG compounds used in the present invention are not limited to those having the same number of carbon atoms. The carbon atoms in Formula (A) are numbered 2 to 7 on the α-chain starting from the α-carbon atom adjacent to the carboxylic carbon atom which is numbered 1 and towards the five-membered ring, 8 to 12 on the said ring starting from the carbon atom on which the α-chain is attached, and 13 to 20 on the α-chain starting from the carbon atom adjacent to the ring. When the number of carbon atoms is decreased in the α-chain, the number is deleted in order starting from position 2 and when the number of carbon atoms is increased in the α-chain, compounds are named as substituted derivatives having respective substituents at position 1 in place of carboxy group (C-1). Similarly, when the number of carbon atoms is decreased in the ω-chain, the number is deleted in order starting from position 20 and when the number of carbon atoms is increased in the ω-chain, compounds are named as substituted derivatives having respective substituents at position 20. Stereochemistry of the compounds is the same as that of above formula (A) unless otherwise specified. Thus, 15-keto-PG compounds having 10 carbon atoms in the ω-chain is nominated as 15-keto-20-ethyl-PGs.

The above formula expresses a specific configuration which is the most typical one, and in this specification compounds having such a configuration are expressed without any specific reference to it.

In general, PGDs, PGEs and PGFs have a hydroxy group on the carbon atom at position 9 and/or 11 but in the present specification the term "15-keto-PG compounds" includes PGs having a group other than a hydroxyl group at position 9 and/or 11. Such PGs are referred to as 9-dehydroxy-9-substituted-PG compounds or 11-dehydroxy-11-substituted-PG compounds.

As stated above, nomenclature of 15-keto-PG compounds is based upon the prostanoic acid. These compounds, however, can also be named according to the IUPAC naming system. For example, 13,14-dihydro-15-keto16R,S-fluoro-PGE$_2$ is (Z)-7-{(1R,2R,3R)-3-hydroxy-2-[(4R,S)-fluoro-3-oxo-1-octyl]-5-oxocyclopentyl}-hept-5-enoic acid. 13,14-dihydro-15-keto-16,16-difluoro-PGE$_2$ is (Z)-7-[(1R,2R,3R)-2-(4,4-difluoro-3-oxo-1-octyl-3-hydroxy5-oxocyclopentyl]-hept-5-enoic acid. 13,14-dihydro-15-keto20-ethyl-11-dehydroxy-11R-methyl-PGE$_2$ methyl ester is methyl 7-{(1R,2S,3S)-3-methyl-2-[3-oxo-1-decyl]-5-oxocyclopenty}hept-5-enoate. 13,14-dihydro-6,15-diketo-19-methyl-PGE$_2$ ethyl ester is ethyl 7-{(1R,2S,3S)-3-hydroxy-2-(7-methyl-3-oxo-1-octyl)-5-oxocyclopentyl}-6-oxo-heptanoate. 13,14-dihydro-15-keto-20-ethyl-PGF$_{2\alpha}$isopropyl ester is isopropyl (Z)-7-[(1R,2R,3R,5S)-3,5-dihydroxy-2-{3-oxo-1-decyl)-cyclopentyl]-hept-5-enoate. 13,14-dihydro-15-keto20-methyl-PGF$_{2\alpha}$methyl ester is methyl (Z)-7-[(1R,2R,3R,5S)3,5-dihydroxy-2-{3-oxo-1-nonyl}-cyclopentyl]-hept-5-enoate.

Preferred Compounds

The 15-keto-PG compounds used in the present invention may be any derivatives of PG insofar as they have an oxo group at position 15 in place of the hydroxy group, and may have a double bond between positions 13 and 14 (15-keto-PG subscript 1 compounds), two double bonds between positions 13 and 14 as well as positions 5 and 6 (15-keto-PG subscript 2 compounds), or three double bonds between positions 13 and 14, positions 5 and 6 as well as positions 17 and 18 (15-keto-PG subscript 3 compounds), and may have a single bond between positions 13 and 14 (13,14-dihydro-15-keto-PG compounds).

Typical examples of the compounds used in the present invention are 15-keto-PGA, 15-keto-PGD, 15-keto-PGE, 15-keto-PGF, 13,14-dihydro-15-keto-PGA, 13,14-dihydro-15-keto-PGD, 13,14-dihydro-15-keto-PGE, and 13, 14-dihydro-15-keto-PGF, wherein PG is as defined above as well as their substitution products or derivatives.

Examples of substitution products or derivatives include esters at the carboxy group at the alpha chain, pharmaceutically or physiologically acceptable salts, unsaturated derivatives having a double bond or a triple bond between positions 2 and 3 or positions 5 and 6, respectively, substituted derivatives having substituent(s) on carbon atom(s) at position 3, 5, 6, 16, 17, 19 and/or 20 and compounds having lower alkyl or a hydroxy (lower) alkyl group at position 9 and/or 11 in place of the hydroxy group, of the above PGs.

Examples of substituents present in preferred compounds are as follows: Substituents on the carbon atom at position 3, 17 and/or 19 include lower alkyl, for example, C$_{1-4}$ alkyl, especially methyl and ethyl. Substituents on the carbon atom at position 16 include lower alkyl e.g. methyl, ethyl etc., hydroxy and halogen atom e.g. chlorine, fluorine, aryloxy e.g. trifluoromethylphenoxy, etc. Substituents on the carbon atom at position 20 include saturated and unsaturated lower alkyl e.g. C$_{1-4}$ alkyl, lower alkoxy e.g. C$_{1-4}$ alkoxy and lower alkoxy (lower) alkyl e.g. C$_{1-4}$ alkoxy-C$_{1-4}$ alkyl Substituents on the carbon atom at position 5 include halogen atom e.g. chlorine, fluorine etc. Substituents on the carbon atom at position 6 include oxo group forming carbonyl. Stereochemistry of PGs having hydroxy, lower alkyl or lower (hydroxy) alkyl substituent on the carbon atom at position 9 and/or 11 may be alpha, beta or mixtures thereof.

Said derivatives may have an alkoxy, phenoxy or phenyl group at the end of the omega chain where the chain is shorter than the primary PGs.

Especially preferred compounds are those having a lower alkyl e.g. methyl, ethyl etc., a halogen atom e.g. chloro, fluoro etc. at position 16, those having a halogen atom e.g. chloro, fluoro etc. at position 17, those having a lower alkyl e.g. methyl, ethyl etc. at position 19, those having a halogen atom e.g. chlorine, fluorine etc. at position 5, those having an oxo group at position 6, those having a lower alkyl, e.g. methyl, ethyl, etc. at position 20 and those having phenyl or phenoxy which are optionally substituted with halogen or haloalkyl at position 16 in place of the rest of the alkyl chain.

A group of preferred compounds used in the present invention has the formula

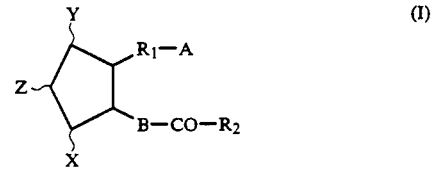

(I)

wherein

X and Y are hydrogen, hydroxy, halo, lower alkyl, hydroxy(lower)alkyl, or oxo, with the proviso that at least one of X and Y is a group other than hydrogen, and 5-membered ring may have at least one double bond, Z is hydrogen or halo, A is —CH$_2$OH, —COCH$_2$OH, —COOH or its functional derivative, B is —CH$_2$—CH$_2$, —CH═CH— or —C≡C—, R$_1$ is bivalent saturated or unsaturated, lower or medium aliphatic hydrocarbon residue which is unsubstituted or substituted with halo, oxo or aryl, R$_2$ is saturated or unsaturated, lower or medium aliphatic hydrocarbon residue which is unsubstituted or substituted with halo, hydroxy, oxo, lower alkoxy, lower alkanoyloxy, cyclo(lower)alkyl, aryl or aryloxy.

In the above formula, the term "unsaturated" in the definitions for R$_1$ and R$_2$ is intended to include at least one and optionally more than one double bond and/or triple bond isolatedly, separately or serially present between carbon atoms of the main and/or side chains. According to usual nomenclature, an unsaturation between two serial positions is represented by denoting the lower number of said two positions, and an unsaturation between two distal positions is represented by denoting both of the positions. Preferred unsaturation is a double bond at position 2 and a double or triple bond at position 5.

The term "lower or medium aliphatic hydrocarbon residue" refers to a straight or branched chain hydrocarbyl group having 1 to 14 carbon atoms (for a side chain, 1 to 3 carbon atoms being preferred) and preferably 2 to 8 carbon atoms for $R_1$ and 6 to 12 carbon atoms for $R_2$.

The term "halo" denotes fluoro, chloro, bromo and iodo.

The term "lower" throughout the specification is intended to include a group having 1 to 6 carbon atoms unless otherwise specified.

The term "lower alkyl" as a group or a moiety in hydroxy(lower)alkyl includes saturated and straight or branched chain hydrocarbon radicals containing 1 to 6, carbon atoms, e.g. methyl, ethyl, propyl, isopropyl, butyl, isobutyl, t-butyl, pentyl and hexyl.

The term "lower alkoxy" refers to the group loweralkyl-O- wherein lower alkyl is as defined above.

The term "hydroxy(lower)alkyl" refers to lower alkyl as defined above which is substituted with at least one hydroxy group, e.g. hydroxymethyl, 1-hydroxyethyl, 2-hydroxyethyl and 1-methyl-1-hydroxyethyl.

The term "lower alkanoyloxy" refers to a group of the formula: RCO-O- wherein RCO- is an acyl group formed by oxidation of a lower alkyl group as defined above, e.g. acetyl.

The term "cyclo(lower)alkyl" refers to a cyclic group formed by cyclization of a lower alkyl group as defined above.

The term "aryl" includes unsubstituted or substituted aromatic carbocyclic or heterocyclic (preferably monocyclic) groups, e.g. phenyl, tolyl, xylyl and thienyl. Examples of substituents are halo and halo(lower)alkyl wherein halo and lower alkyl being as defined above.

The term "aryloxy" refers to a group of the formula: ArO- wherein Ar is aryl as defined above.

The term "functional derivative" of carboxy as A includes salts (preferably pharmaceutically acceptable salts), esters and amides.

Suitable "pharmaceutically acceptable salts" includes conventional non-toxic salts, and may be a salt with an inorganic base, for example an alkali metal salt (e.g. sodium salt, potassium salt, etc.) and an alkaline earth metal salt (e.g. calcium salt, magnesium salt, etc.), ammonium salt, a salt with an organic base, for example, an amine salt (e.g. methylamine salt, dimethylamine salt, cyclohexylamine salt, benzylamine salt, piperidine salt, ethylenediamine salt, ethanolamine salt, diethanolamine salt, triethanolamine salt, tris(hydroxymethylamino)ethane salt, monomethyl-monoethanolamine salt, procaine salt, caffeine salt, etc.), a basic amino acid salt (e.g. arginine salt, lysine salt, etc.), tetraalkyl ammonium salt and the like. These salts can be prepared by the conventional process, for example from the corresponding acid and base or by salt interchange.

Examples of the esters are aliphatic esters, for example, lower alkyl ester e.g. methyl ester, ethyl ester, propyl ester, isopropyl ester, butyl ester, isobutyl ester, t-butyl ester, pentyl ester, 1-cyclopropylethyl ester, etc., lower alkenyl ester e.g. vinyl ester, allyl ester, etc., lower alkynyl ester e.g. ethynyl ester, propynyl ester, etc., hydroxy(lower) alkyl ester e.g. hydroxyethyl ester, lower alkoxy(lower)-alkyl ester e.g. methoxymethyl ester, 1-methoxyetyl ester, etc., and aromatic esters, for example, optionally substituted aryl ester e.g. phenyl ester, tosyl ester, t-butylphenyl ester, salicyl ester, 3,4-di-methoxyphenyl ester, benzamidophenyl ester etc., aryl(lower)alkyl ester e.g. benzyl ester, trityl ester, benzhydryl ester, etc. Examples of the amides are mono- or di- lower alkyl amides e.g. methylamide, ethylamide, dimethylamide, etc., arylamide e.g. anilide, toluidide, and lower alkyl- or aryl-sulfonylamide e.g. methylsulfonylamide, ethylsulfonylamide, tolylsulfonylamide etc.

Preferred examples of A include —COOH, -COOCH$_3$, —COOCH$_2$CH$_3$, —COOCH(CH$_3$)$_2$ and —CONHSO$_2$CH$_3$.

The configuration of the ring and the α- and/or omega chain in the above formula (I) may be the same as or different from that in the primary PGs. However, the present invention also includes a mixture of a compound having a primary configuration and that of an unprimary configuration.

Examples of the typical compounds of the present invention are 15-keto-PGs, 13,14-dihydro-15-keto-PGs and their e.g. 6-keto-derivatives, $\Delta^2$-derivatives, 3R,S-methyl-derivatives, 5R,S-fluoro-derivatives, 5,5-difluoro-derivatives, 16R,S-methyl-derivatives, 16,16-dimethyl-derivatives, 16R,S-fluoro-derivatives, 16,16-difluoro-derivatives, 17S-methyl-derivatives, 17R,S-fluoro-derivatives, 17,17-difluoro-derivatives, 19-methyl-derivatives, 20-methyl-derivatives, 20-ethyl-derivatives, 19-desmethyl-derivatives and 16-desbutyl-16-phenoxy derivatives.

When 15-keto-PG compounds of the present invention have a saturated bond between positions 13 and 14, these compounds may be in the keto-hemiacetal equilibrium by forming a hemiacetal between hydroxy group at position 11 and ketone at position 15.

The proportion of both tautomeric isomers, when present, varies depending on the structure of the rest of the molecule or kind of any substituent present and, sometimes, one isomer may predominantly be present in comparison with the other. However, in this invention, it is to be appreciated that the compounds used in the invention include both isomers. Further, while the compounds used in the invention may be represented by a structure or name based on keto-form regardless of the presence or absence of the isomers, it is to be noted that such structure or name does not intend elimination of the hemiacetal type of compounds.

In the present invention, any of the individual tautomeric isomers, a mixture thereof, or optical isomers, a mixture thereof, a racemic mixture, and other isomers such as steric isomers can be used in the same purpose.

Some of the compounds used in the present invention may be prepared by the method disclosed in Japanese Patent Publications (unexamined) No. A-52753/1989, A-104040/1989, A-151519/1989.

Alternatively, these compounds may be prepared by a process analogous to that described herein or to known processes.

A practical preparation of the 15-keto compounds involves the following steps; referring to the Synthetic Charts I to III, reaction of the aldehyde (2) prepared by the Collins oxidation of commercially available (—)-Corey lactone (1) with dimethyl (2-oxoheptyl)phosphate anion to give α,β-unsaturated ketone (3), reduction of the α,β-unsaturated ketone (3) to the corresponding saturated ketone (4), protection of the carbonyl group of the ketone (4) with a diol to the corresponding ketal (5), and deprotection of the p-phenylbenzoyl group to give the corresponding alcohol (6) followed by protection of the newly derived hydroxy group with dihydropyrane to give the corresponding tetrahydropyranyl ether (7). According to the above process, a precursor of PGEs wherein the ω-chain is a 13,14-dihydro-15-keto-alkyl group is prepared.

Using the above tetrahydropyranyl ether (7), 6-keto-PGE₁s (15) of which a group constituted with carbon atoms at positions 5. 6 and 7 is

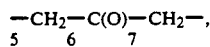

may be prepared in the following steps; reduction of the tetrahydropyranyl ether (7) with, for example, diisobutyl aluminum hydride to give the corresponding lactol (8), reaction of the lactol (8), with the ylide generated from (4-carboxybutyl)triphenyl phosphonium bromide followed by esterification (10), cyclization between the 5,6-double bond and the hydroxyl group at position 9 with NBS or iodine to give the halogenated compound (11), dehydrohalogenation of the compound (11) with, for example, DBU to give the 6-keto compound (13) followed by Jones oxidation and removal of the protecting groups.

Furthermore, PGE₂s (19) of which a group constituted with carbon atoms at positions 5, 6 and 7 is

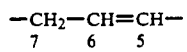

may be prepared in the following steps; as shown in the Synthetic Chart II, reduction of the above tetrahydropyranyl ether (7) to give the lactol (8), reaction of the resultant lactol (8) with the ylide derived from (4-carboxybutyl-)triphenyl phosphonium bromide to give the carboxylic acid (16) followed by esterification to give ester (17), Jones oxidation of the esters (17) to give the compound (18), and removal of the protecting groups.

Using the above tetrahydropyranyl ether (7) as the starting material, the compound having

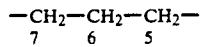

may be prepared by using the same process as that for preparing PGE₂ having —CH₂CH=CH— and subjecting the resultant compound (18) to catalytic reduction to reduce the double bond between the positions 5 and 6 followed by removal of the protective groups.

Synthesis of 5,6-dehydro-PGE₂s having

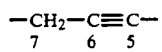

may be carried out by capturing a copper enolate formed by 1,4-addition of a monoalkylcopper complex or a dialkylcopper complex of the following formulae:

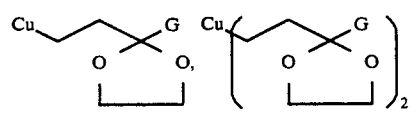

wherein G is alkyl, to 4R-t-butyldimethylsilyloxy-2-cyclopenten-1-one with 6-alkoxycarbonyl-1-iodo-2-hexyne or the derivatives.

The 11-β type PGEs can be prepared according to the Synthetic Chart III.

PGE derivatives having a methyl group at position 11 in place of hydroxy can be prepared by reacting a dimethyl copper complex with PGA-type compound obtained by subjecting 9-hydroxy-11-tosylate to the Jones oxidation. Alternatively, they can be prepared by protecting the carbonyl of saturated ketone (4) produced by reducing unsaturated ketone (3), eliminating p-phenylbenzoyl and tosylating the produced alcohol, treating with DBU to form a lactol, introducing the alpha-chain by Wittig reaction, oxidizing the alcohol at position 9 to give PGA-type compound, and reacting the product with dimethyl copper complex in order to introduce a methyl group into position 11 to give an 11-methyl-PGE-type compound, which on reduction with e.g. sodium borohydride gives an 11-methyl-PGF-type compound. An 11-hydroxymethyl-PGE-type compound, is obtained by a benzophenone-sensitized photoaddition of methanol of PGA-type compound, which is reduced with, e.g. sodium borohydride, to give an 11-hydroxymethyl-PGF-type compound. The 16-mono- or 16,16-di-halo type PGEs can be prepared according to the synthetic chart IV. The synthetic route for the compounds used in the present invention is not limited to the that described above one and may vary using different protecting, reducing and/or oxidizating methods.

Corresponding other PG compounds can be produced analogously.

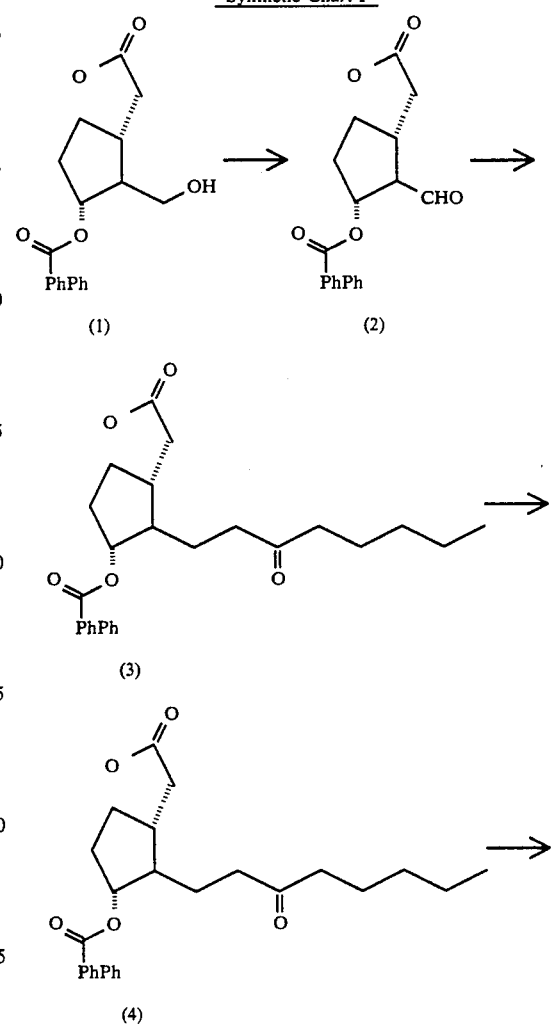

Synthetic Chart I

-continued
Synthetic Chart I
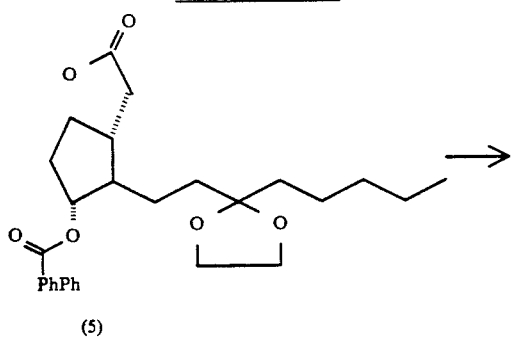
(5)
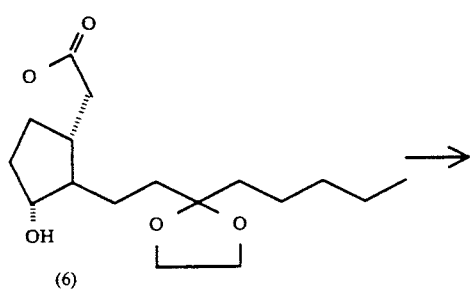
(6)
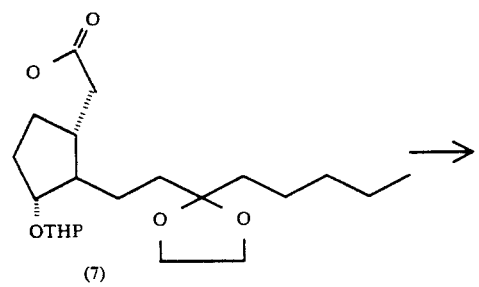
(7)
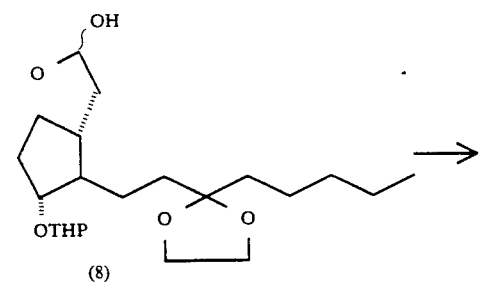
(8)
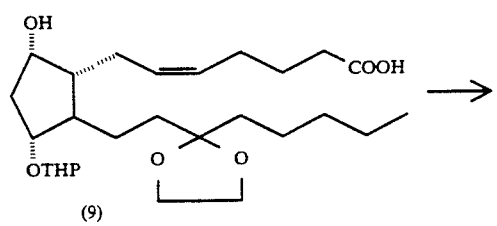
(9)
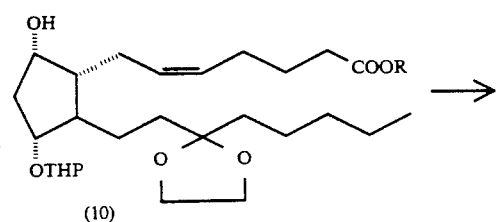
(10)
-continued
Synthetic Chart I
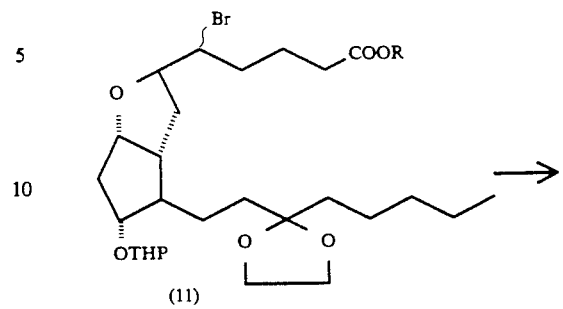
(11)
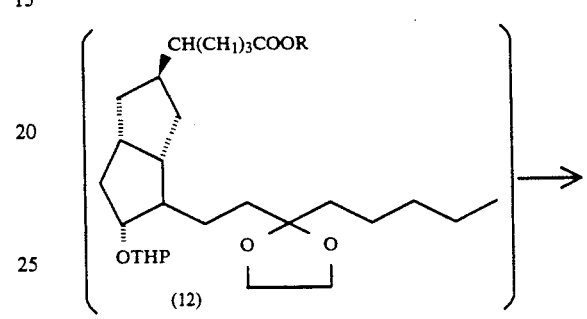
(12)
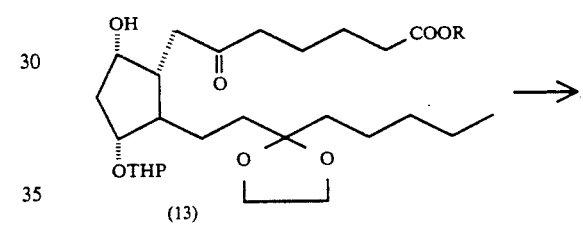
(13)
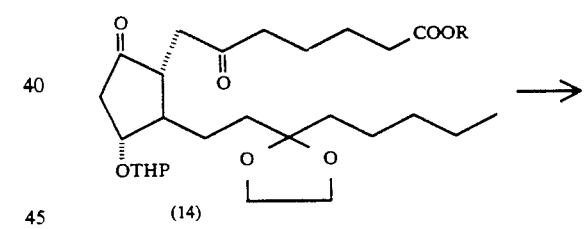
(14)
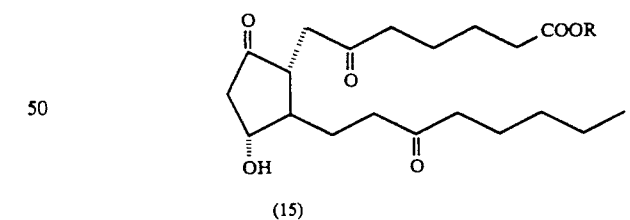
(15)
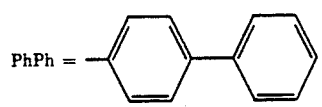
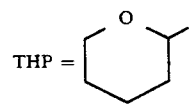
R = lower alkyl Synthetic Chart II
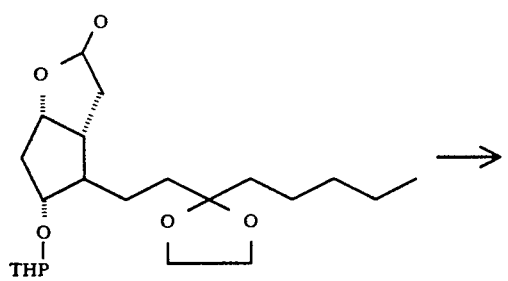
(7)
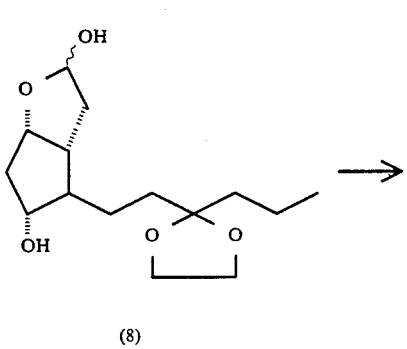
(8)
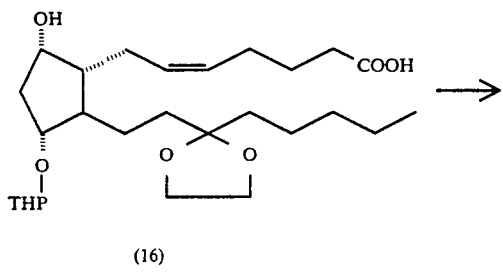
(16)
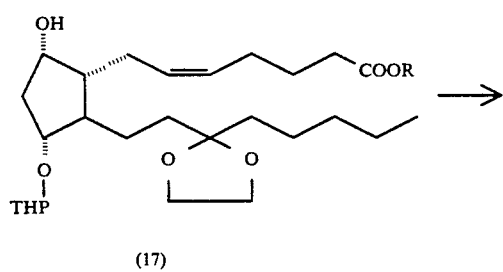
(17)
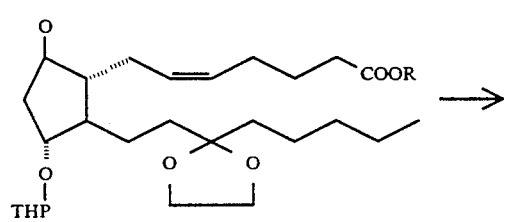
(18)
-continued
Synthetic Chart II
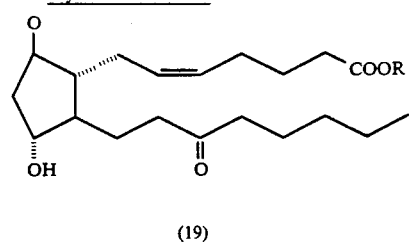
(19)
Synthetic Chart III
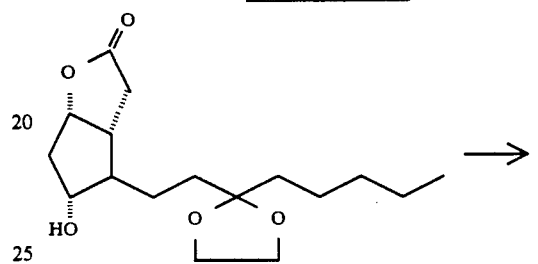
(6)
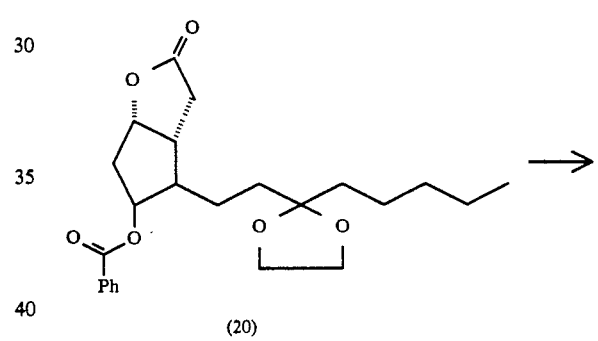
(20)
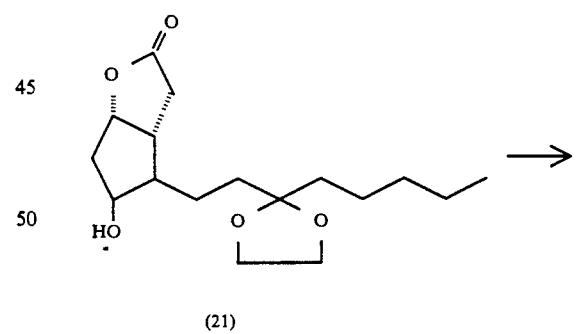
(21)
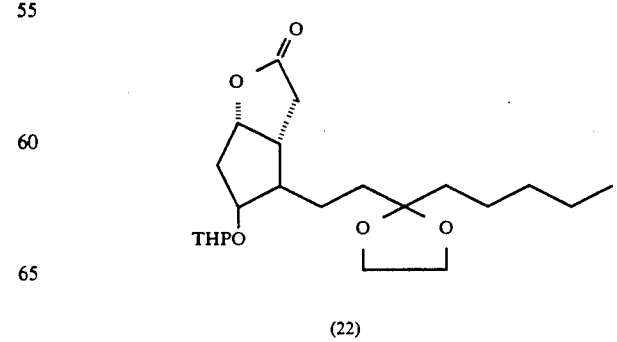
(22)

5,256,696
13
-continued
Synthetic Chart III
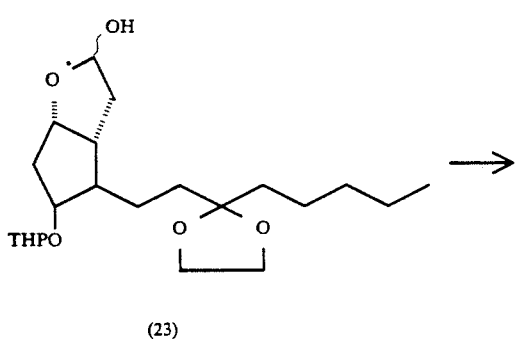
(23)
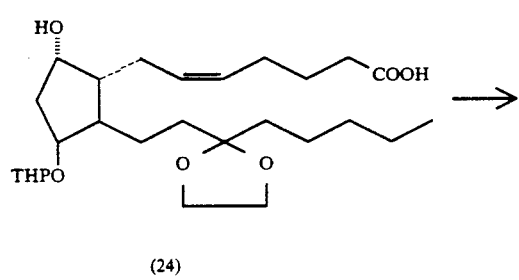
(24)
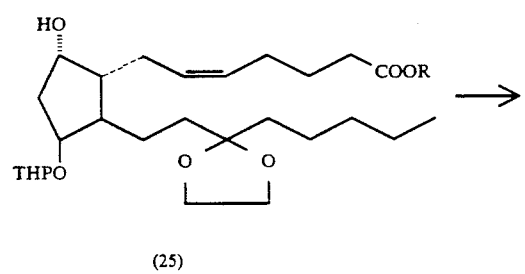
(25)
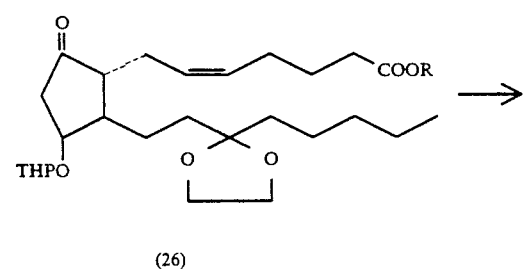
(26)
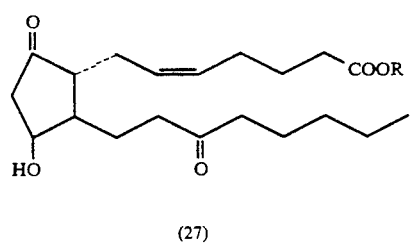
(27)
14
Synthetic Chart IV
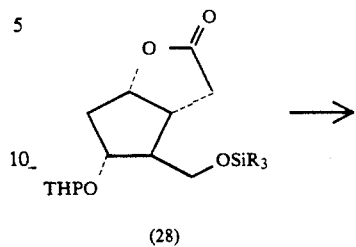
(28)
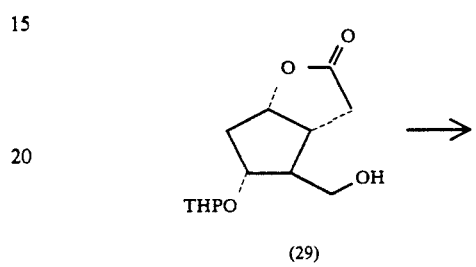
(29)
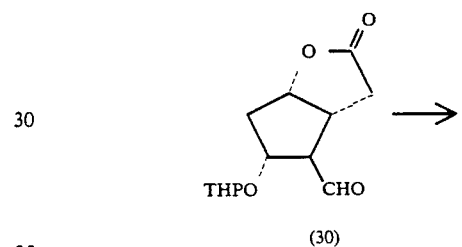
(30)
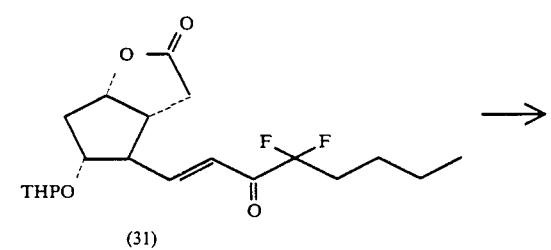
(31)
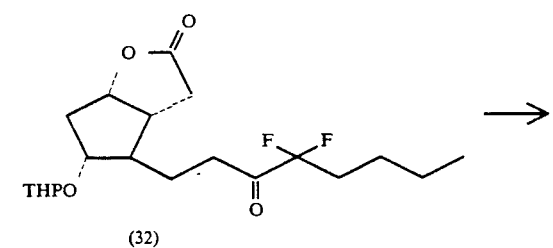
(32)
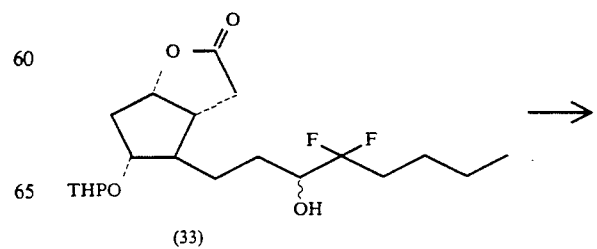
(33)

-continued
Synthetic Chart IV

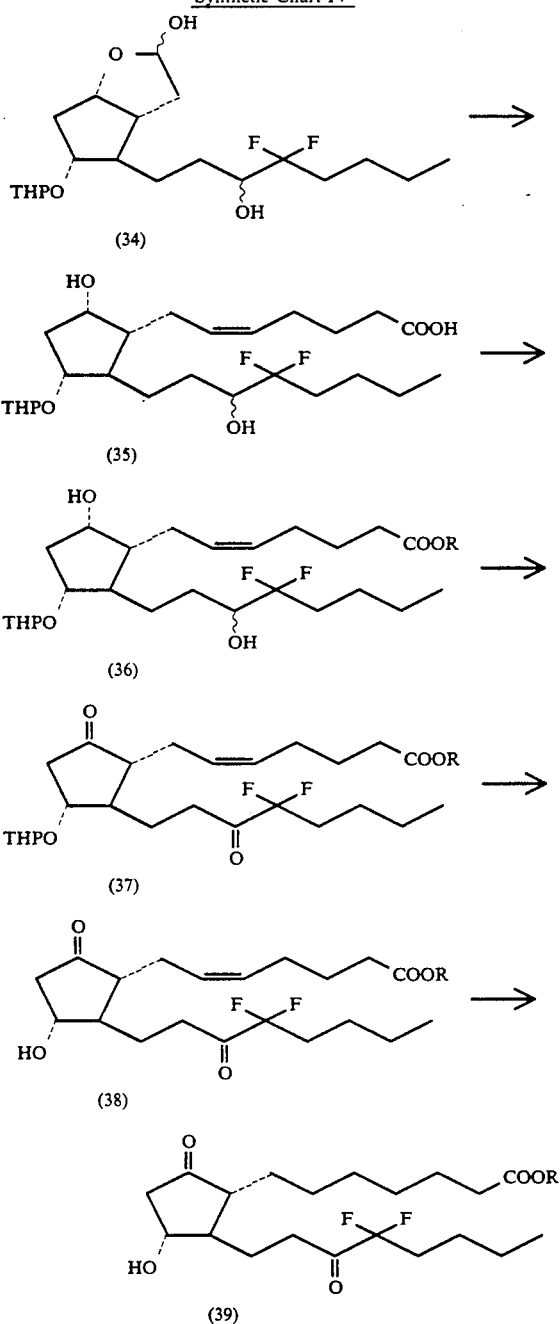

Since the compounds used in the present invention have an activity useful for preventing or curing cardiac dysfunction, these can be used for preparing a medicament for treating cardiac dysfunction. Such activities can be measured by the standard methods such as contraction of isolated atrial preparation.

The compounds used in the present invention may be used as a medicine for animals and human beings and usually applied systemically or locally by such methods as oral administration, intravenous injection (including instillation), subcutaneous injection, suppository and the like. While the dosage will vary depending on the particular animal or human patient, age, body weight, symptom to be treated, desired therapeutic effect, administration route, term of treatment and the like, satisfactory effects will be obtained with the dosage of 0.001–500 mg/kg administered in 2 to 4 divided doses a day or as a sustained form.

As a solid composition of this invention for oral administration, tablets, troches, buccals, capsules, pills, powders, granules and the like are included. The solid composition containing one or more active substances is mixed with at least an inactive diluent, e.g. lactose, mannitol, glucose, hydrocypropyl cellulose, fine crystalline cellulose, starch, polyvinyl pyrolidone, magnesium aluminate metasilicate. The composition may contain additives other than the inactive diluent, for example, lubricants e.g., magnesium stearate, a disintegrator e.g. cellulose calcium gluconates, stabilizers e.g. $\alpha$-, $\beta$- or $\gamma$-cyclodextrins, etherated cyclodextrins (e.g. dimethyl-$\alpha$-, dimethyl-$\beta$-,trimethyl-$\beta$-, or hydroxypropyl-$\beta$-cyclodextrins), branched cyclodextrins (e.g. glucosyl- or maltosyl-cyclodextrins), formyl cyclodextrins, sulfur-containing cyclodextrins, misoprotols or phospholipids. Such cyclodextrins may increase the stability of the compounds by forming an inclusion compounds. The stability may be often increased by forming lyposome with phospholipids. Tablets and pills may be coated with an enteric or gastroenteric film e.g. white sugar, gelatin, hydroxypropylcellulose, hydroxypropylmethylcellulose phthalates and the like, if necessary, and furthermore they may be covered with two or more layers. Additionally, the composition may be in the form of capsules made of substance easily absorbed e.g. gelatin. The composition may be in the form of buccals, when an immediate effect is desired. For this purpose, base e.g. glycerine, lactose may be used.

Liquid compositions for oral administration include pharmaceutically acceptable emulsions, solutions, suspensions, syrups, elixirs and the like and contain a generally used inactive diluent e.g. purified water or ethyl alcohol. The composition may contain additives e.g. wetting agents, suspending agents, sweeteners, flavors, perfumes and preservatives.

The composition of the present invention may be in the form of sprays which may contain one or more active ingredients and which can be prepared according to a well known methods.

An injection of this invention for non-oral administration includes serile aqueous or nonaqueous solutions, suspensions, and emulsions. Diluents for the aqueous solution or suspension include, for example, distilled water for injection, physiological saline and Ringer's solution. Diluents for the nonaqueous solution and suspension include, for example, propylene glycol, polyethylene glycol, vegetable oils e.g. olive oil, alcohols, e.g. ethanol and polysorbates. The composition may contain other additives, e.g. preservatives, wetting agents, emulsifying agents, dispersing agents and the like. These are sterilized by filtration through, e.g. a bacteria-retaining filter, compounding with a sterilizer, gas sterilization or radiation sterilization. These can be prepared by producing a sterilized water or a sterilized solvent for injection before use.

Another formulation according to the present invention is a rectal or vaginal suppository. This can be prepared by mixing at least one active compound according to the invention with a suppository base e.g. cacao butter and optionally containing nonionic surfactant for improving absorption.

A more complete understanding of the present invention can be obtained by reference to the following Preparation Examples, Formulation Examples and Test Examples which are provided herein for purpose of illustration only and are not intended to limit the scope of the invention.

PREPARATION EXAMPLE 1

Preparation of 16,16-difluoro-13,14-dihydro-15-keto-PGE$_1$ methyl ester (39)

1-1) Preparation of (1S,5R,6R,7R)-6-hydroxymethyl-7-tetrahydropyranyloxy-2-oxabicyclo[3.3.0]octan-3-one (29)

To a solution of commercial Corey lactone (THP-form, 37.9g) in tetrahydrofuran was added a solution (1.0 M, 300 ml) of tetrabutylammonium fluoride in tetrahydrofuran and the resulting mixture was stirred at room temperature for 3 hours.

Then the reaction mixture was concentrated under reduced pressure and the residue was subjected to column chromatography to give the title compound (29). Yield: 21.70g (82.8%).

1-2) Preparation of (1S,5R,6R,7R)-6-{(E)-4,4-difluoro-5-oxo-2-octenyl}-7-tetrahydropyranyloxy-2-oxabicyclo[3,3,0]octan-3-one (31)

A solution (2.0 M, 45.5 ml) of oxalyl chloride in methylene chloride was diluted with methylene chloride under an argon atmosphere at −78° C. To this solution was added dropwise dimethylsulfoxide (12.9 ml) and the resulting mixture was stirred for 10 minutes. A solution (1S,5R,6R,7R)-6-hydroxymethyl-7-tetrahydropyranyloxy-2-oxabicylo[3.3.0]octan-3-one (29) (11.65 g) in methylene chloride was added dropwise and the mixture was stirred for 30 minutes. Then triethylamine (56 ml) was added dropwise and stirring was continued for further 1 hour. The reaction mixture was treated in the conventional manner to give the aldehyde (30) as a crude product.

To a solution of thallium ethoxide (3.26 ml) in methylene chloride was added under an argon atmosphere dimethyl 3,3-difluoro-2-oxoheptylphosphonate (11.9 g) and the resulting mixture was stirred for 1 hour. After cooling the solution to 0° C., a solution of the aldehyde (30) obtained above in methylene chloride was added dropwise to said solution and the mixture was stirred at room temperature for 14 hours. The reaction mixture was treated with acetic acid, celite and a saturated aqueous potassium idodide solution and filtered. The filtrate was treated in the conventional manner and the crude product was subjected to column chromatography to give the tile compound (31). Yield: 7.787 g (44.3 %).

1-3) Preparation of (1S,5R,6R,7R)-6-(4,4-difluoro-5-oxooctyl)-7-tetrahydropyranyloxy-2-oxabicyclo[3.3.0]octan-3-one (32)

To a solution of (1S,5R,6R,7R)-6-{(E)-4,4-difluoro-5-oxo-2-octenyl}-7-tetrahydropyranyloxy-2-oxabicyclo[3.3.0]octan-3-one (31) (5.57 g) in ethyl acetate was added 5% Pd/C (catalytic amount) and the resulting mixture was shaken under a hydrogen atmosphere at room temperature for 7 hours. The reaction mixture was filtered and the filtrate was concentrated under reduced pressure to give the tile compound (32) as a crude product. Yield: 5.48 g (97.8%).

1-4) Preparation of (1S,5R,6R,7R)-6-{4,4-difluoro-5(RS)-hydroxyoctyl}-7-tetrahydropyranyloxy-2-oxabicyclo[3.3.0]-octan-3-one (33)

To a solution of (1S,5R,6R,7R)-6-(4,4-difluoro-5-oxooctyl)-7-tetrahydropyranyloxy-2-oxabicyclo[3.3.0]octan-3-one (32) (5.48 g) in methanol was added sodium borohydride (0.800 g) at 0° C. and the resulting mixture was stirred for 10 minutes. The reaction mixture was treated in the conventional manner and the obtained crude product was subjected to column chromatography to give the title compound (33). Yield: 5.46 g (99.5%).

1-5) Preparation of 16,16-difluoro-13,14-dihydro-11-O-tetrahydropyranyl-PGF$_{2\alpha}$methyl ester (36)

A solution of (1S,5R,6R,7R)-6-{4,4-dihydro-5(RS)-hydroxyoctyl}-7-tetrahydropyranyloxy -2-oxabicyclo[3.3.0]-octan-3-one (33) (2.579 g) in toluene was cooled to −78° C. under an argon atmosphere. To this solution was added dropwise a solution (1.5 M, 9.6 ml) of diisobutylalmium hydride in toluene and stirred for 30 minutes. The reaction mixture was treated with methanol and a saturated aqueous Rochelle salt solution. Then the solution was treated in the conventional manner to give the lactol (34) as a crude product.

To a suspension of 4-carboxybutyl triphenyl phosphine bromide (11.72 g) in tetrahydrofuran was added dropwise under an argon atmosphere a solution (1.0 M, 52.84 ml) of potassium tert-butoxide in tetrahydrofuran and the resulting mixture was stirred for 20 minutes. The solution was cooled to 0° C. and combined with a solution of lactol (34) in tetrahydrofuran. The resulting mixture was stirred at room temperature for 15 hours and then treated in the conventional manner to give the carboxylic acid (35) as a crude product.

To a solution of the carboxylic acid (35) in acetonitrile was added under an argon atmosphere 1,8-diazabicyclo[5.4.0]undec-7-ene (DBU) (4.0 ml) and methyl iodide (1.7 ml) and the resulting solution was stirred at 60° C. for 30 hours. The solution was treated in the conventional manner and the product was subjected to column chromatography to give the title compound (36). Yield: 2.737 g (84.5%).

1-6) Preparation of 16,16-difluoro-13,14-dihydro-15-keto-11-O-tetrahydropyranyl-PGE$_2$ methyl ester (37)

To a solution of Collins reagent, prepared from cromic anhydride (16.18 g) and pyridine (26.2 ml) in the conventional process, in methylene chloride was added a solution of 16,16-difluoro-13,14-dihydro-11-0-tetrahydro-pyranyl-PGF$_{2\alpha}$methyl ester (36) (2.646 g) in methylene chloride under an argon atmosphere at −20° C. The resulting mixture was stirred at the same temperature for 2 hours and at −5° C. for 9 hours. The solution was treated with ether and sodium hydrogen sulfate and filtered. The filtrate was concentrated under reduced pressure and the residue was subjected to column chromatography to give the title compound (37). Yield: 1.890 g (64.4%).

1-7) Preparation of 16,16-difluoro-13,14-dihydro-15-ketoPGE$_2$ methyl ester (38)

Into a mixed solvent of acetic acid : water : tetrahydrofuran (3:1:1) was dissolved 16,16-difluoro-13,14-dihydro-15-keto-11-O-tetrahydroxypyranyl-PGE$_2$ methyl ester (37) (2.809 g) and the resulting solution was stirred at 60° C. for 5 hours. The reaction mixture was concentrated under reduced pressure and the residue was subjected to chromatography to give the title compound (38). Yield: 1.755 g (75.5%).

1-8) Preparation of 16,16-difluoro-13,14-dihydro-15-keto-PGE$_1$ methyl ester (39)

To a solution of 16,16-difluoro-13,14-dihydro-15-keto-PGE$_2$ methyl ester (38) (1.755 g) in ethyl acetate was added Pd/C (catalytic amount) and the mixture was shaken under a hydrogen atmosphere at room temperature for 6 hours. The reaction mixture was filtered. The filtrate was concentrated and the residue was subjected to column chromatography to give the title compound (39). Yield: 1.655 g (93.8%).

$^1$H NMR(CDCl$_3$) δ0.87(3H,t,J=7Hz), 1.15-2.05(23H,m), 2.11-2.30(3H,m), 2.50(1H,dd,J=7.5 and 17Hz), 3.10-3.20 (1H,br), 3.71(3H,s), 4.05-4.20(1H,m) MS(DI-EI) m/z 404(M+) 355 (M+—H$_2$O—CH$_3$O), 297(M+—C$_5$H$_9$F$_2$)

Preparation Example 2

Preparation of 16,16-difluoro-13,14-dihydro-15-keto-PGE$_1$ (39')

2-1) Preparation of (15RS)-16,16-difluoro-13,14-dihydro-11-O-tetrahydropyranyl-PGF$_{2\alpha}$benzyl ester (36)

To a solution of 16,16-difluoro-13,14-dihydro-11-O-tetrahydropyranyl-PGF$_{2\alpha}$(35) (2.33 g) in dichloromethane (300 ml) were added DBU (2.1 ml) and benzyl bromide (2.2 ml) and the resulting mixture was stirred at room temperature for 1.5 hour. The reaction mixture was treated in the conventional manner and the crude product was purified by silica-gel column chromatography to give the title compound (36). Yield: 2.522 g (96.1%)

2-2) Preparation of 16,16-difluoro-13,14-dihydro-15-keto-11-O-tetrahydropyranyl-PGE$_2$ benzyl ester (37)

Collins reagent was prepared by using chromic anhydride (13.5 g) and pyridine (21.8 ml) in dichloromethane (300 ml), and to this were added Celite (40 g) and (15RS)16,16-difluoro-13,14-dihydro-11-O-tetrahydropyranyl-PGF$_{2\alpha}$benzyl ester (36) (2.550 g). The reaction mixture was treated in the conventional manner and the crude product was purified by silica-gel column chromatography to give the title compound (37). Yield: 1.991 g (78.6%) 2-3) Preparation of 16,16-difluoro-13,14-dihydro-15-ketoPGE$_2$ benzyl ester (38)

Into a mixed solvent of acetic acid:THF:water (3:1:1, 50 ml) was dissolved 16,16-difluoro-13,14-dihydro15-keto-11-O-tetrahydropyranyl-PGE$_2$ benzyl ester (37) (1.550 g) and the solution was kept at 50° C. for 4 hours. The reaction mixture was treated in the conventional manner and the crude product was purified by silica-gel column chromatography to give the title compound (38). Yield: 1.225g (92.9%)

2-4) Preparation of 16,16-difluoro-13,14-dihydro-15-ketoPGE$_1$ (39')

To a solution of 16,16-difluoro-13,14-dihydro-15-keto-PGE$_1$ benzyl ester (38) (0.844 g) in ethyl acetate (30 ml) was added 5% Pd/C and the mixture was shaken under a hydrogen atmosphere. The reaction mixture was treated in the conventional manner and the crude product was purified by silica-gel column chromatography to give the title compound (43). Yield: 0.404 g $^1$H NMR(CDCl$_3$) δ0.94 (t,3H,J=7.5 Hz), 1.20-2.70 (m,26H), 4.19 (m,1H), 4.80 (br,2H).

MS(DI-EI) m/z 390(M+) 372(M+—H$_2$O), 354(M+—2H$_2$O)

Formulation Example 1

(Powders for injection)

|  | (Parts by weight) |
|---|---|
| 13,14-dihydro-15-keto-16,16-difluoro-PGE$_2$ | 1 |
| mannitol | 5 |
| distilled water | 0.4 |

The above ingredients were mixed, stirred, sterilized, filtered and lyophilized to give powders for injection.

Formulation Example 2

(Injectable solution)

|  | (Parts by weight) |
|---|---|
| 13,14-dihydro-15-keto-16,16-difluoro-PGE$_1$ | 0.2 |
| nonion surfactant | 2 |
| distilled water | 98 |

The above ingredients were mixed and sterilized to give and injectable solution.

Formulation Example 3

(Enteric capsules)

13,14-dihydro-15-keto-16,16-difluoro-20-methylPGE$_2$(50mg) dissolved in methanol (10ml) was mixed with mannitol (18.5g). The mixture was screened (with a sieve, the pore size of which being 30 mm in diameter), dried at 30° C for 90 minutes and screened again. The powders thus obtained were mixed with fine-grain silica gel (Aerosil*, 200g) and filled in No.3 hard gelatin capsules (100) to give enteric capsules which contain 0.5mg of 13,14-dihydro-15-keto-16,16-difluoro-20-methyl-PGE$_2$ per capsule.

*Trade Mark

Formulation Example 4

(Powders for oral administration)

|  | (Parts by weight) |
|---|---|
| 13,14-dihydro-6,15-diketo-16,16-difluoro-PGE$_1$ methyl ester | 5 |
| light anhydrous silicic acid | 5 |
| Abicel* | 20 |
| lactose | 70 |

The above ingredients were mixed to give powders for oral administration.
*Trade Mark

Formulation Example 5

|  | (Parts by weight) |
|---|---|
| 13,14-dihydro-6,15-diketo-19-methyl-PGE$_1$ methyl ester | 1 |
| light anhydrous silicic acid | 899 |
| Panasate* | 20 |

The above ingredients were mixed and filled in soft gelatine capsules.
*Trade Mark

Formulation Example 6

(Enteric capsules)

16-desbutyl-13, 14-dihydro-15-keto-16-m-trifluoormethylphenoxy-PGF$_{2\alpha}$methyl ester (50mg) dissolved in methanol (10ml) was mixed with mannitol (18.5g). The mixture was screened (with a sieve, the pore size of which being 30 mm in diameter), dried at 30° C. for 90 minutes and screened again. The powders thus obtained were mixed with fine-grain silica gel (Aersoil*, 200g) and filled in No. 3 hard gelatin capsules (100) to give enteric capsules which contain 0.5mg of 13, 14-dihydro-15-keto-16-desbutyl-16-m-trifluroemethylphenoxy-PGF$_{2\alpha}$methyl ester per capsule. ≠Trade Mark

Formulation Example 7

|  | (Parts by weight) |
|---|---|
| 13,14-dihydro-15-keto-16,16-difluoro-$PGE_1$ | 1 |
| mannitol | 5 |
| distilled water | 0.4 |

The above ingredients were mixed, stirred, sterilized, filtered and lyophilied to give powders for injection.

Formulation Example 8

|  | (Parts by weight) |
|---|---|
| 13,14-dihydro-6,15-diketo-5R,S-difluoro-$PGE_1$ | 0.2 |
| nonion surfactant | 2 |
| distilled water | 98 |

The above ingredients were mixed and sterilized to give and injectable solution.

Formulation Example 9

(Powders for oral administration)

|  | (Parts by weight) |
|---|---|
| 13,14-dihydro-15-keto-16,16-difluoro-19-desmethyl-$PGE_2$ methyl ester | 5 |
| light anhydrous silicic acid | 5 |
| Abicel* | 20 |
| lactose | 70 |

The above ingredients were mixed to give powders for oral administration.
*Trade Mark

Formulation Example 10

(Soft gelatine capsules)

|  | (Parts by weight) |
|---|---|
| 13,14-dihydro-15-keto-16-desbutyl-16-m-trifluoromethylphenoxy-$PGE_2$ methyl ester | 1 |
| light anhydrous silicic acid | 899 |
| Panasate* | 20 |

The above ingredients were mixed and filled in soft gelatine capsules.
*Trade Mark In the above formulation examples, the active ingredient can be replaced by any other compound within the compounds used in the invention.

Test Example 1

The atria of hearts were removed from guinea pigs (Hartley strain, male, 400-500 g) and suspended in the Krebs-Hensleite solution (50 ml) at 36° C bubbled with a mixed gas consisting of 95% $O_2$ and 5% $CO_2$. Change in tension of atria was recorded on a recorder by introducing to strain-pressure amplifier via an FD pick-up loaded with strain of about 0.5 g. The recording was continued for 10 minutes after the application of test compounds.

The test compounds were cumulatively administered as a solution (5 μl) dissolved in ethanol (final concentration: 0.01%). No change in contraction was observed by administration of 0.01 % ethanol.

The results are shown in Table 1 as an increase in contraction as compared with that of control which received vehicle alone.

TABLE 1

| Test Compound | Contraction at | |
|---|---|---|
|  | $1 \times 10^{-6}$ M | $1 \times 10^{-5}$ M |
| 1 | +17.0% | +26.0% |
| 2 | +15.0% | +33.0% |
| 3 | +6.0% | +21.0% |
| 4 | — | +11.3% |
| 5 | +29.0% | — |
| 6 | +12.7% | +32.8% |
| 7 | +13.5% | — |
| 8 | +27.5% | — |

Test Compounds:
1: 13,14-dihydro-15-keto-16,16-difluoro-$PGE_2$
2: 13,14-dihydro-15-keto-16R,S-fluoro-$PGE_2$
3: 13,14-dihydro-6,15-diketo-19-methyl-$PGE_1$ ethyl ester
4: 13,14-dihydro-6,15-diketo-5,5-difluoro-$PGE_1$ methyl ester
5: 13,14-dihydro-15-keto-16,16-difluoro-11-dehydroxy-11-methyl-$PGE_2$ methyl ester
6: 13,14-dihydro-15-keto-16,16-difluoro-$PGE_1$
7: 13,14-dihydro-15-keto-16,16-difluoro-$PGA_2$ methyl ester
8: 13,14-dihydro-15-keto-16,16-difluoro-$PGD_2$ methyl ester In the following data, NMR spectra were measured in $CDCl_3$ using HITACHI R-90H and mass spectra were measured by EI method at an ionization potential of 70eV using -HITACHI M-80B.

*13,14-dihydro-15-keto-16,16-difluoro-$PGE_2$
$^1H$ NMR ($CDCl_3$) δ0.93(t,3H,J=7.5 Hz), 1.20-2.70(m,24H), 4.20 (m,1H), 5.40(m,2H)
MS(DI-EI) m/z 388(M+) 370(M+—$H_2O$), 352(M+—$2H_2O$)

*13,14-dihydro-6,15-diketo-5,5-difluoro-$PGE_1$ methyl ester
$^1H$ NMR ($CDCl_3$) δ0.88(t,3H,J=6.6 Hz), 1.10-1.40(m,4H), 1.45-2.20(m,10H) 2.20-3.15(m,11H), 3.67(s,3H), 4.00-4.18 (m,1H)
MS(DI-EI) m/z 418(M+), 400(M+—$H_2O$), 360(M+—HF—$H_2O$), 99($C_6H_{11}CO+$)

*13,14-dihydro-15-keto-16,16-difluoro-11-dehydroxy-11-methyl-$PGE_2$ methyl ester
$^1H$ NMR ($CDCl_3$) δ0.93(t,3H,J=7.5 Hz), 1.14(d,3H,J=6 Hz), 1.25-2.80(m,22H), 3.68(s,3H), 5.38(m,2H)
MS(DI-EI) m/z 400(M+) 369(M+—$CH_3O$)

*13,14-dihydro-15-keto-16,16-difluoro-$PGA_2$ methyl ester
$^1H$ NMR ($CDCl_3$) δ0.93(t,3H,J=7.5 Hz), 1.20-2.85(m,20H), 3.68 (s,3H), 5.41(m,2H), 6.19(dd,1H,J=2.5 and 1.2 Hz), 7.58 (dd,1H,J=2.5 and 1.2 Hz)
MS(DI-EI) m/z 384(M+) 353(M+—$CH_3O$)

*13,14-dihydro-15-keto-16,16-difluoro-$PGD_2$ methyl ester
$^1H$ NMR ($CDCl_3$) δ0.91(t,3H,J=7.5 Hz), 1.20-3.20(m,23H), 3.68 (s,3H), 4.44(m,1H,J=1.2 Hz), 5,49(m,2H)
MS(DI-EI) m/z 402(M+), 384(M+—$H_2O$), 353(M+—$H_2O$ —$CH_3O$)

The above results clearly show that the compounds used in the invention have an effect increasing contraction of cardiac muscle.

Test Example 2

(Method)

A female Beagle dog (weight : 11 kg) was anesthetized with pentobarbital (25 mg/kg, i.v.) and the maintenance dosages of pentobarbital for anesthesia were appropriately administered. The dog was fixed in the left-side-up lateral position and a cannula was inserted into the trachea. The respirations were controlled with an artificial respiration. The blood pH and $pCO_2$ was maintained within the normal region. The dog was subjected to thoracotomy at the fourth intercostal space. The aorta was carefully exfoliated over about 2 cm from the starting point and equipped with an electromagnetic flowmeter (MFW-3200, Nihon Koden), which was connected to a bioelectric amplifier (AB-621G, Nihon Koden), on which the cardiac output was measured.

A test compound (13,14-dihydro-15-keto-16,16-difluoro-$PGE_2$) was dissolved in the physiological saline and administered at a dosage of 10 μg/kg over 30 seconds through a polyethylene tube inserted in cephalic vein. The cardiac output was observed for 30 minutes. The control value was obtained by administering the physiological saline alone.

(Results)

When the physiological saline was administered, the cardiac output (maximum) was varied from 0.82 to 0.89 l/min (8.5%), while, with the test compound, it was increased from 0.66 to 0.85 l/min (29%).

What is claimed is:

1. A method for treatment of a cardiac dysfunction which comprises administering, to a subject in need of such treatment, a cardiac dysfunction treatment effective amount of a 15-ketoprostaglandin compound represented by formula (I):

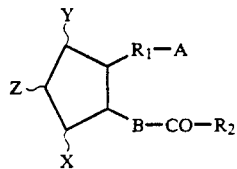

(I)

wherein

X and Y are hydrogen, hydroxy, halo, lower alkyl, hydroxy(lower)alkyl, or oxo, with the proviso that at least one of X and Y is a group other than hydrogen, and 5-membered ring may have at lest one double bond, Z is hydrogen or halo, A is —CH$_2$OH, —COCH$_2$OH, —COOH or its functional derivative, B is —CH$_2$—Ch$_2$, —CH=CH— or —C≡C—, R$_1$ is bivalent saturated or unsaturated, lower or medium aliphatic hydrocarbon residue which is unsubstituted or substituted with halo, oxo or aryl, R$_2$ is saturated or unsaturated, lower or medium aliphatic hydrocarbon residue which is unsubstituted or substituted with halo, hydroxy, oxo, lower alkoxy, lower alkanoyloxy, cyclo(lower)alky, aryl or aryloxy, and said compound represented by formula (I) having at least one of (i) a halogen atom at position 5 or 16 or at positions 5 and 16 and (ii) a lower alkyl at position 19.

2. The method according to claim 1, in which the cardiac dysfunction is based on increase in myocardial contractility.

3. The method according to claim 1, in which said 15-ketoprostaglandin compound is a 16-mono- or di-halo-15-ketoprostaglandin compound.

4. The method according to claim 1, in which said 15-ketoprostaglandin compound is a 13,14-dihydro-16-mono- or di-halo-15-ketoprostaglandin compound.

5. The method according to claim 1, in which said 15-ketoprostaglandin compound is a 13,14-dihydro-16-mono- or di-fluoro-15-ketoprostaglandin compound.

6. The method according to claim 1, in which said 15-ketoprostaglandin compound is a 6,15-diketoprostaglandin compound.

7. The method according to claim 1, in which said 15-ketoprostaglandin compound is a 13,14-dihydro-6,15-diketo-prostaglandin compound.

8. The method according to claim 1, in which said 15-ketoprostaglandin compound is a 15-keto-19-alkyl-prostaglandin compound.

9. The method according to claim 1, in which said 15-ketoprostaglandin compound is a 13,14-dihydro-15-keto-19-alkyl-prostaglandin compound.

10. The method according to claim 1, wherein said cardiac dysfunction is a condition having etiology based on or accompanied by insufficiency of cardiac function.

11. The method according to claim 1, wherein said cardiac dysfunction is a symptom or disease based on unbalance between the cardiac output and the peripheral demand resulting from disorder of myocardial contractive and dilative functions.

12. The method according to claim 1, wherein said cardiac dysfunction is a symptom or disease selected from orthopnea, dyspnea, pulmonary congestion, hepatic congestion, cardipalmus, sensation of precordial compression, heart contusion, arrhythmia, angina pectoris, myocardial infarction, atrial fibrillation, atrial flutter and paroxysmal tachycardia.

13. The method according to claim 1, wherein said treatment comprises control of cardiac dysfunction in a mammal, including preventing the disease, curing the disease, relieving the disease and arresting or relieving the development of the disease.

14. The method according to claim 1, wherein said 15-ketoprostaglandin compound is administered in an amount of 0.001-500 mg/kg in 2 to 4 divided doses a day or as a sustained form.

* * * * *